United States Patent
Deavenport et al.

(10) Patent No.: US 9,220,670 B2
(45) Date of Patent: *Dec. 29, 2015

(54) ETHERS WITH MONOCATIONIC POLYHYDROXYL FUNCTIONALITY

(75) Inventors: Joseph L. Deavenport, Lake Jackson, TX (US); Nicole A. Brehm, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/006,746

(22) PCT Filed: Apr. 20, 2012

(86) PCT No.: PCT/US2012/034441
§ 371 (c)(1),
(2), (4) Date: Sep. 23, 2013

(87) PCT Pub. No.: WO2012/145621
PCT Pub. Date: Oct. 26, 2012

(65) Prior Publication Data
US 2014/0030208 A1  Jan. 30, 2014

Related U.S. Application Data

(60) Provisional application No. 61/477,851, filed on Apr. 21, 2011.

(51) Int. Cl.
| | | |
|---|---|---|
| *A61K 8/41* | (2006.01) | |
| *A61Q 19/00* | (2006.01) | |
| *A61Q 5/12* | (2006.01) | |
| *C07C 217/08* | (2006.01) | |
| *A61Q 5/00* | (2006.01) | |

(52) U.S. Cl.
CPC . *A61K 8/416* (2013.01); *A61Q 5/00* (2013.01); *A61Q 5/12* (2013.01); *A61Q 19/00* (2013.01); *C07C 217/08* (2013.01); *A61K 2800/10* (2013.01)

(58) Field of Classification Search
None
See application file for complete search history.

(56) References Cited

U.S. PATENT DOCUMENTS

| | | |
|---|---|---|
| 6,177,577 B1 | 1/2001 | Roerden et al. |
| 6,869,977 B1 | 3/2005 | O'Lenick et al. |
| 7,176,172 B2 | 2/2007 | Harding et al. |
| 7,214,806 B2 | 5/2007 | Lang et al. |
| 7,282,471 B2 | 10/2007 | Harichian et al. |
| 7,541,496 B2 | 6/2009 | Deavenport et al. |
| 7,659,234 B2 | 2/2010 | Harichian et al. |
| 2010/0021960 A1 | 1/2010 | Rotello et al. |
| 2013/0178542 A1* | 7/2013 | Deavenport et al. ......... 514/788 |

FOREIGN PATENT DOCUMENTS

| | | | |
|---|---|---|---|
| DE | 4238213 A1 | | 5/1994 |
| PL | 136722 | * | 3/1986 |
| WO | 9733882 A1 | | 9/1991 |
| WO | 2007025093 A2 | | 3/2007 |
| WO | 2008145410 A1 | | 12/2008 |

OTHER PUBLICATIONS

Ingredients of Cosmetics, entry for Bishydroxyethyl Dihydroxypropyl stearammonium chloride, http://ingredientsofcosmetics.com/ingredient/bishydroxyethyrl%20dihydroxypropyrl%20stearammonium%20chloride, Feb. 19, 2009.*
Klopotek, et al., Preparation of 3-Ammonio-2-Hydroxypropyl Alkaneddicarboxylates, Aug. 13, 1981. Abstract only.
Morris-Natschke, et al., Synthesis of Phosphocholine and Quaternary Amine Ether Lipids and Evaluation of in Vitro Antineoplastic Activity, Journal of Medicinal Chemistry, American Chemical Society, vol. 36, No. 14, 1993, pp. 2018-2025.
Chen, et al., Synthesis and Evaluation of novel Thymidine Analogsas Antitumor and Antiviral Agents, Journal of Medicinal Chemistry, vol. 39, No. 17, 1996, pp. 3412-3417.
Arch Personal Care Product Brochure—Honeyquat 50 Substantive Honey Derivative, Jan. 2004.
Colonial Chemical, Inc. Product Brochure—Cola® Moist 300P, 2007.
Colonial Chemical, Inc. Product Brochure—Cola® Moist 200, 2008.
Semioshkin, et al., Synthesis and Structure of Novel Closo-Dodecaborate-Based Glycerols, Journal of Organometallic Chemistry, vol. 695, No. 3, 2010, pp. 370-374.
Meyer, et al.; J.Med. Chem. 1991, 34, 1377-1383.

* cited by examiner

*Primary Examiner* — Mina Haghighatian
*Assistant Examiner* — Erin Hirt
(74) *Attorney, Agent, or Firm* — Edward L. Brant

(57) ABSTRACT

Described are novel monocationic polyhydroxyl compounds and their uses in personal care compositions.

19 Claims, No Drawings

ETHERS WITH MONOCATIONIC POLYHYDROXYL FUNCTIONALITY

CROSS REFERENCE TO RELATED APPLICATIONS

This application is a 35 USC §371 national phase filing of PCT/US2012/034441 filed Apr. 20, 2012, which claims the benefit of U.S. Application No. 61/477,851, filed Apr. 21, 2011.

FIELD

The present invention relates to novel monocationic polyhydroxyl compounds and their uses in personal care compositions.

BACKGROUND

Polyhydroxyl compounds, or polyols, have a number of uses, from raw materials used in the manufacture of urethane foams to humectants for personal care products like shaving foams, lotions, and shampoos.

Quaternary ammonium compounds are also useful in a number of applications, such as for disinfectants, surfactants, fabric softeners, and conditioners in shampoos.

Despite the number of available conventional compounds, there is a strong need for novel compounds with properties to differentiate performance or offer synergistic effects in areas of interest, particularly in personal care compositions.

DETAILED DESCRIPTION

In one embodiment, the present invention provides compounds, including salts, of the Formula (I):

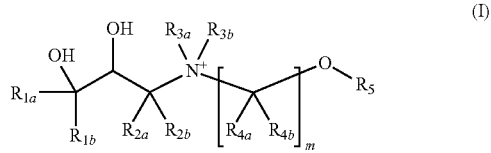

(I)

wherein:
wherein:
m is 1, 2, 3, 4, 5, or 6;
$R_{1a}$, $R_{1b}$, $R_{2a}$, $R_{2b}$, $R_{4a}$, and $R_{4b}$, are, independently at each occurrence, H, optionally substituted C1-C6 alkyl; and
$R_{3a}$, $R_{3b}$ and $R_5$ are, independently, optionally substituted C1-C6 alkyl.

The term "optionally substituted" as used herein means that the groups in question are either unsubstituted or substituted with one or more groups, radicals or moieties, selected from halogen, hydroxy, amino or carboxy. When the groups in question are substituted with more than one substituent, the substituents may be the same or different. In one embodiment, the optional substituent is selected to produce a cosmetically acceptable compound. "Cosmetically acceptable" refers to ingredients typically used in personal care compositions, and is intended to underscore that materials that are toxic, irritating, or unpleasant smelling when present in the amounts typically found in personal care compositions are not contemplated as part of the present invention. In one embodiment, the optional substituent is hydroxy.

"Alkyl" means a saturated monovalent linear or branched aliphatic hydrocarbon radical. Representative examples include, but are not limited to methyl, ethyl, propyl, isopropyl, butyl, isobutyl, tert-butyl, sec-butyl, pentyl, isopentyl, neopentyl, hexyl, isohexyl, and the like.

The term "cycloalkyl" denotes a saturated monocyclic or bicyclic cycloalkyl group. Examples of cycloalkyl groups include cyclopropyl, cyclobutyl, cyclopentyl, cyclohexyl, cycloheptyl, cyclooctyl, and the like. In one embodiment, the cycloalkyl is cyclohexyl or cyclopentyl.

Salts means that a counter-ion is present, preferably halogen, more preferably $Cl^-$.

In one embodiment, m is 2, 3, or 4. Preferably, m is 2.

In some embodiments, $R_{4a}$ and $R_{4b}$ are H at each occurrence. In some embodiments, at least one $R_{4a}$ is —$CH_3$, —$CH_2OH$, or —$CH_2CH_3$. Alternatively, $R_{4a}$ and $R_{4b}$ may cooperate, along with the carbon to which they are attached, to form a cycloalkyl group.

In a preferred embodiment, $R_5$ is —$CH_2CH_2OH$.

In one embodiment, $R_{1a}$ and $R_{1b}$ are each H.

In one embodiment, $R_{2a}$ and $R_{2b}$ are each H.

In some embodiments, $R_{3a}$ and $R_{3b}$ are the same. Examples of such embodiments include those where $R_{3a}$ and $R_{3b}$ are each —$CH_3$, those where $R_{3a}$ and $R_{3b}$ are each —$CH_2CH_3$, and those where $R_{3a}$ and $R_{3b}$ are each —$CH_2CH_2OH$.

Alternatively, in some embodiments, $R_{3a}$ and $R_{3b}$ are not the same. Examples of such embodiments include those where $R_{3a}$ is —$CH_2CH_2OH$. In one embodiment, $R_{3a}$ is —$CH_2CH_2OH$ and $R_{3b}$ is —$(CH_2)_3CH_3$.

Non-limiting examples of compounds of Formula I include the reaction products of 3-chloro-1,2-propanediol and amino ether alcohols. Non-limiting examples of these include 2-(2-dimethylamino)ethoxyethanol, 2-[2-(diethylamino)ethoxylethanol, 2-[2-(dimethylamino)-1-methylethoxy]ethanol, and Ethyl(2-hydroxyethyl)[2-(2-hydroxyethoxy)ethyl]amine.

In one embodiment, the present invention provides methods for providing humectancy in a personal care composition, comprising including the compound of Formula I into the personal care composition. The ingredients used, and their proportions and manner of addition, are familiar to those versed in conventional personal care compositions, including, optionally, cosmetically acceptable emollients, moisturizers, conditioners, oils, sunscreens, surfactants, emulsifiers, preservatives, rheology modifiers, colorants, preservatives, pH adjustors, propellants, reducing agents, fragrances, foaming or de-foaming agents, tanning agents, depilatory agents, astringents, antiseptics, deodorants, antiperspirants, insect repellants, bleaches, tighteners, anti-dandruff agents, adhesives, polishes, strengtheners, fillers, barrier materials, or biocides.

In one embodiment, the present invention provides hair care compositions containing the compound of Formula I.

In one embodiment, the present invention provides skin care compositions containing the compound of Formula I.

EXAMPLES

The following examples are for illustrative purposes only and are not intended to limit the scope of the present invention.

Example 1

Reaction of 3-chloro-1,2-propanediol and 2-[2-(dimethylamino)ethoxy]ethanol to afford 2,3-dihydroxy-N-(2-(2-hydroxyethoxy)ethyl)-N,N-dimethylpropan-1-aminium chloride

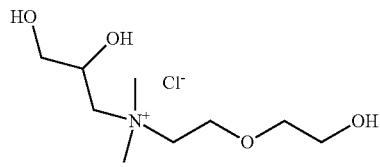

A 250 mL round bottom, jacketed, flask was equipped with a magnetic stir bar and placed on a stir-plate. The temperature was set to about 25° C. and monitored with a thermocouple. 48.84 g 2-(2-dimethylamino)ethoxyethanol (98% purity, 0.36 mole) was combined with 49.05 g deionized water and allowed to mix for about fifteen minutes before commencing the addition of 40.32 g 3-chloro-1,2-dihydroxypropane (99.6% purity, 0.36 mole) over 1 hour at 25° C. The reaction solution was allowed to stir for about 1 hour at 25° C. and then for about 4 hours at 45° C. (hot digest). After the hot digest step was completed, the circulation bath was turned off and solution was allowed to cool. At this time, the pH was adjusted to 7.1 with 0.02 moles of HCl.

$^{13}C$ NMR spectra acquired from a Bruker 300 MHz spectrometer (samples prepared as ~30 wt % in $D_2O$) confirmed the title compound: DEPT NMR (250 MHz, $D_2O$) 54.9, 62.7, 66.1, 66.5, 66.7, 68.5, 69.3, 74.1

Example 2

Reaction of 3-chloro-1,2-propanediol and 2-[2-(diethylamino)ethoxy]ethanol to afford N,N-diethyl-2,3-dihydroxy-N-(2-(2-hydroxyethoxy)ethyl)propan-1-aminium chloride

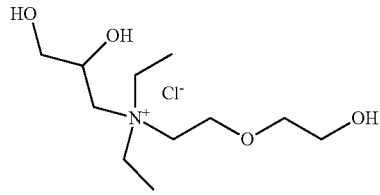 [SMILES: CC[N+](CC)(CCOCCO)CC(O)CO ; [Cl-]]

The title compound is prepared substantially according to the protocol of Example 1, except that the conditions and amounts of reactants may vary, typically a 1:1 mol ratio with a slight excess of 3-chloro-1,2-propanediol, but which factors are well within the skill of one ordinarily skilled in the art.

Example 3

Reaction of 3-chloro-1,2-propanediol and Ethyl(2-hydroxyethyl)[2-(2-hydroxyethoxy)ethyl]amine to afford N-ethyl-2,3-dihydroxy-N-(2-(2-hydroxyethoxy)ethyl)-N-(2-hydroxyethyl)propan-1-aminium chloride

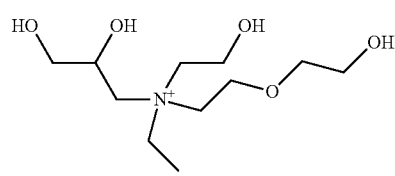 [SMILES: CC[N+](CCO)(CCOCCO)CC(O)CO]

The title compound is prepared substantially according to the protocol of Example 1, except that the conditions and amounts of reactants may vary, typically a 1:1 mol ratio with a slight excess of 3-chloro-1,2-propanediol, but which factors are well within the skill of one ordinarily skilled in the art.

Example 4

Reaction of 3-chloro-1,2-propanediol and 2-[2-(dimethylamino)-1-methylethoxy]ethanol to afford 2,3-dihydroxy-N-(2-(2-hydroxyethoxy)propyl)-N,N-dimethylpropan-1-aminium chloride

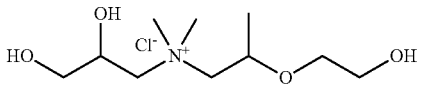

The title compound is prepared substantially according to the protocol of Example 1, except that the conditions and amounts of reactants may vary, typically a 1:1 mol ratio with a slight excess of 3-chloro-1,2-propanediol, but which factors are well within the skill of one ordinarily skilled in the art.

Example 5

Compounds prepared substantially according to the Examples 1-4 are made and formulated into personal care compositions having otherwise conventional ingredients. The compositions are evaluated by trained panelists, with each panelist being asked to compare the inventive compositions to a conventional composition.

For hair care compositions, wet and dry feel preference and wet and dry combability is measured by asking the panelists to feel and comb two hair tresses of European virgin brown hair, commercially available from International Hair Importers and Products Inc. NY (USA), one hair tress treated with an inventive composition, the other hair tress treated with a conventional composition. Each panelist is asked to compare the tresses and state which tress is smoother to comb/feel. The answer "same" is not allowed. The reported number is the percent of panelists preferring one over the other.

For skin care compositions, panelists apply a sample (one inventive composition, one conventional composition) to a designated area on their right or left forearm. Initially, each sample is evaluated for ease of application, play time, evenness of deposit, coverage, speed of adsorbtion, shine, matte, skin moistness, heaviness, amount of grease, amount of tack, quickness of drying, overall skin feel, and overall appearance. After a designated time, each sample is again evaluated, this time for coverage, evenness of coverage, shine, matte, skin moistness, heaviness, and overall appearance.

It is understood that the present invention is not limited to the embodiments specifically disclosed and exemplified herein. Various modifications of the invention will be apparent to those skilled in the art. Such changes and modifications may be made without departing from the scope of the appended claims. Moreover, each recited range includes all combinations and subcombinations of ranges, as well as specific numerals contained therein. Additionally, the disclosures of each patent, patent application, and publication cited or described in this document are hereby incorporated herein by reference, in their entireties.

The invention claimed is:

1. A salt comprising an ion of the Formula (I):

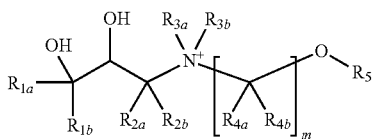

(I)

wherein:
  m is 1, 2, 3, 4, 5, or 6;
  $R_{1a}$, $R_{1b}$, $R_{2a}$, $R_{2b}$, $R_{4a}$, and $R_{4b}$, are, independently at each occurrence, H, optionally substituted C1-C6 alkyl, or $R_{4a}$ and $R_{4b}$ cooperate to form a cyclohexyl group; and
  $R_{3a}$, $R_{3b}$ and $R_5$ are, independently, C1-C6 alkyl which is optionally substituted,
wherein if m is 2, 3, 4, 5, or 6, then $R_{4a}$ and $R_{4b}$ may, independently at each occurrence, be the same or different, provided that at least one of (1) at least one occurrence of $R_{4a}$ is —CH$_2$OH, (2) at least one occurrence of $R_{4a}$ and $R_{4b}$ cooperate to form a cyclohexyl group, and (3) $R_{3a}$ and $R_{3b}$ are each —CH$_2$CH$_2$OH.

2. The salt of claim 1, wherein m is 2, 3, or 4.

3. The salt of claim 1, wherein at least one occurrence of $R_{4a}$ is CH$_3$.

4. The salt of claim 1, wherein at least one occurrence of $R_{4a}$ is —CH$_2$OH.

5. The salt of claim 1, wherein at least one occurrence of $R_{4b}$ is —CH$_2$CH$_3$.

6. The salt of claim 1, wherein at least one occurrence of $R_{4a}$ and $R_{4b}$ cooperate to form a cyclohexyl group.

7. The salt of claim 1, wherein $R_5$ is —CH$_2$CH$_2$OH.

8. The salt of claim 1, wherein $R_{1a}$ and $R_{1b}$ are each H.

9. The salt of claim 1, wherein $R_{2a}$ and $R_{2b}$ are each H.

10. The salt of claim 1, wherein $R_{3a}$ and $R_{3b}$ are the same.

11. The salt of claim 10, wherein $R_{3a}$ and $R_{3b}$ are each —CH$_3$.

12. The salt of claim 10, wherein $R_{3a}$ and $R_{3b}$ are each —CH$_2$CH$_3$.

13. The salt of claim 10, wherein $R_{3a}$ and $R_{3b}$ are each —CH$_2$CH$_2$OH.

14. The salt of claim 1, wherein $R_{3a}$ and $R_{3b}$ are not the same.

15. The salt of claim 14, wherein $R_{3a}$ is —CH$_2$CH$_2$OH.

16. The salt of claim 15, wherein $R_{3b}$ is —(CH$_2$)$_3$CH$_3$.

17. A method for providing humectancy in a personal care composition, comprising including the salt of claim 1 into the personal care composition.

18. A hair care composition containing the salt of claim 1.

19. A skin care composition containing the salt of claim 1.

* * * * *